United States Patent
Zhang et al.

(10) Patent No.: US 9,241,816 B2
(45) Date of Patent: Jan. 26, 2016

(54) STENT FOR BIFURCATED VESSEL

(71) Applicant: Shanghai MicroPort Medical (Group) Co., Ltd., Shanghai (CN)

(72) Inventors: Dadong Zhang, Shanghai (CN); Yan Li, Shanghai (CN); Changchun Wang, Shanghai (CN); Zhirong Tang, Shanghai (CN); Qiyi Luo, Shanghai (CN)

(73) Assignee: Shanghai MicroPort Medical (Group) Co., Ltd., Shanghai (CN)

( * ) Notice: Subject to any disclaimer, the term of this patent is extended or adjusted under 35 U.S.C. 154(b) by 0 days.

(21) Appl. No.: 14/450,955

(22) Filed: Aug. 4, 2014

(65) Prior Publication Data

US 2014/0343666 A1 Nov. 20, 2014

Related U.S. Application Data

(63) Continuation-in-part of application No. 13/642,623, filed as application No. PCT/CN2011/072972 on Apr. 19, 2011, now abandoned.

(30) Foreign Application Priority Data

Apr. 20, 2010 (CN) .......................... 2010 1 0151612

(51) Int. Cl.
*A61F 2/90* (2013.01)
*A61F 2/915* (2013.01)
*A61F 2/856* (2013.01)
*A61F 2/82* (2013.01)

(52) U.S. Cl.
CPC ................. *A61F 2/915* (2013.01); *A61F 2/856* (2013.01); *A61F 2002/821* (2013.01); *A61F 2002/91558* (2013.01); *A61F 2250/006* (2013.01); *A61F 2250/0098* (2013.01)

(58) Field of Classification Search
CPC ... A61F 2/82; A61F 2/90; A61F 2002/91516; A61F 2002/91525; A61F 2002/9155
See application file for complete search history.

(56) References Cited

U.S. PATENT DOCUMENTS

| 5,653,727 A | 8/1997 | Wiktor |
| 5,893,887 A | 4/1999 | Jayaraman |

(Continued)

FOREIGN PATENT DOCUMENTS

| CN | 1194577 | 9/1998 |
| CN | 2643861 | 9/2004 |

(Continued)

OTHER PUBLICATIONS

Extended European Search Report issued in the corresponding European Application No. EP 11771568, dated May 27, 2015, 6 pages.

*Primary Examiner* — David Isabella
*Assistant Examiner* — Dinah Baria
(74) *Attorney, Agent, or Firm* — Hamre, Schumann, Mueller & Larson, P.C.

(57) ABSTRACT

A stent for a bifurcated vessel includes a stent body (1) with two open ends (5, 6). The stent body (1) includes multiple sets of annular units (2) having multiple undulating rods (4) and connecting rods (3) positioned between adjacent annular units (2) and used to connect the adjacent annular units (2). At least one open end (6) of the stent body (1) has a slope structure.

10 Claims, 5 Drawing Sheets

(56) References Cited

U.S. PATENT DOCUMENTS

| | | |
|---|---|---|
| 5,911,754 A | 6/1999 | Kanesaka et al. |
| 6,264,686 B1 | 7/2001 | Rieu et al. |
| 6,932,837 B2 | 8/2005 | Amplatz |
| 2004/0068314 A1 | 4/2004 | Jones et al. |
| 2004/0186560 A1 | 9/2004 | Alt |
| 2007/0270769 A1 | 11/2007 | Wilson et al. |
| 2008/0015681 A1 | 1/2008 | Wilson et al. |

FOREIGN PATENT DOCUMENTS

| | | |
|---|---|---|
| CN | 2009-48183 | 9/2007 |
| CN | 2009-66659 | 10/2007 |
| JP | 1999-057019 | 3/1999 |
| JP | 2003-527925 | 9/2003 |
| WO | 2007073413 | 6/2007 |
| WO | 2008091515 | 7/2008 |

STENT FOR BIFURCATED VESSEL

BACKGROUND

The present application relates to the implantable medical device field and in particular to a stent for a bifurcated vessel.

A stent for a vessel is generally a drug eluting stent for treating vascular stenosis. The stent for a vessel implanted in the human body assists the lesion vessel in recovering by supporting the lesion vessel. Meanwhile, the stent for a vessel can also release a drug on the stent to the vascular wall in contact therewith to inhibit growth of cells of the vascular wall and reduce the incidence rate of vascular restenosis.

In the clinical practice, with respect to many patients, the vascular stenosis does not occur in only one place but in multiple places in the vessel. The bifurcated lesion vessel is a common multiple artery stenosis. As shown by the shaded portions in FIG. 1, the vascular lesion sites are positioned at the intersection of a main vessel 1 and a branch vessel 2.

In the process of developing the present application, the inventors find that at least the following problems exist in the prior art: 1) as shown in FIG. 2, an existing stent for a branch vessel has a structure with both ends flush, and cannot completely and sufficiently cover the vessel at the lesion sites when treating the bifurcated lesion vessel, thus influencing the treating effect; 2) as shown in FIG. 3, an existing branch vessel adopts the "crush" technique, but the stent for a branch vessel and the stent for a main vessel overlap too much, which results in the amount of the implanted metal being too much, whereby thrombus is likely to be formed at the intersection of the vessels.

SUMMARY

In order to solve the above technical problem, the embodiments of the present application provide a stent for a bifurcated vessel to solve the problem that the existing stents for a bifurcated vessel cannot completely cover the lesion site or overlap at the lesion site after being implanted in the human body. The technical solutions are as follows:

A stent for a bifurcated vessel, comprising a stent body with two open ends, the stent body comprising: multiple sets of annular units having multiple undulating rods; and connecting rods positioned between adjacent annular units and used to connect the adjacent annular units, wherein the structure of at least one open end of the stent body is a slope structure.

Preferably, the number of the undulating rods in the multiple sets of annular units forming the slope structure decreases in turn in a direction from a middle part of the stent body to the open end having the slope structure.

Preferably, the compactness of the undulating rods in the multiple sets of annular units forming the slope structure increases in turn in a direction from a middle part of the stent body to the open end having the slope structure.

Preferably, the number of the undulating rods in the multiple sets of annular units forming the slope structure decreases in turn and the compactness of the undulating rods in the multiple sets of annular units forming the slope structure increases in turn in a direction from a middle part of the stent body to the open end having the slope structure.

Preferably, the axial length of the slope structure is 1~7 mm.

Preferably, the axial length of the slope structure is 4~6 mm.

Preferably, an included angle between the slope surface of the slope structure and the axial direction of the stent body is between 0 degree and 90 degrees.

Preferably, the included angle between the slope surface of the slope structure and the axial direction of the stent body is 45 degrees.

Preferably, at least four developable marks are further provided around the slope surface of the slope structure, wherein at least two developable marks are respectively provided at the top and bottom of the slope surface of the slope structure, and at least two other developable marks are symmetrically provided on both sides of the slope surface along an axial center line.

Preferably, the stent for a bifurcated vessel is a stent for a bifurcated coronary artery.

Preferably, the diameter of the stent for a bifurcated coronary artery is 2.25 mm~4.0 mm.

Preferably, the material of the stent body is a stainless steel, a cobalt-chromium alloy, a nickel-based alloy, a degradable magnesium alloy or a polymer material having good biological compatibility and mechanical characteristics.

Preferably, the top of the slope structure can be also of a smooth arc shape or a flush shape.

In the technical solutions provided by the embodiments of the present application, at at least one end of the stent for a bifurcated vessel, the number of the undulating rods in each set of annular unit is decreased in turn, or the compactness of the undulating rods in each set of annular unit is increased in turn, or the two are performed simultaneously, in a direction from the middle part of the stent body to the open end having the slope structure, to shorten the length of each set of annular unit in turn to form a slope structure. The angle of the slope structure matches with the bifurcation angle of the branch vessel. Thus, the stent for a bifurcated vessel can completely and sufficiently cover the vessel at the lesion site and will not overlap the stent for a main vessel after being implanted in the lesion site of the bifurcated vessel of the human body.

In addition, at least four developable marks are provided around the slope surface of the slope structure of the stent for a bifurcated vessel. In the at least four developable marks, at least two developable marks are respectively provided at the top and bottom of the slope structure, and at least two other developable marks are symmetrically provided on both sides of the slope surface of the slope structure along an axial center line. In the delivering process, the doctor can clearly distinguish the slope surface of the slope structure of the stent for a bifurcated vessel according to the development positions of the developable marks, and then the doctor rotates the stent by rotating a balloon dilatation catheter, so that the slope surface of the slope structure can join the main vessel, and then releases and dilates the stent. Thus, this stent for a bifurcated vessel can be also located accurately in the delivering and releasing process to facilitate the surgical procedure by the doctor.

BRIEF DESCRIPTION OF THE DRAWINGS

In order to describe the technical solutions in the embodiments of the present application or the prior art more clearly, the figures to be used in the descriptions of the embodiments or the prior art will be briefly introduced below. It is obvious that the figures in the descriptions below only relate to some embodiments recorded in the present application, and those skilled in the art can also obtain other figures according to these figures without making inventive efforts.

DETAILED DESCRIPTION

Figure 1:
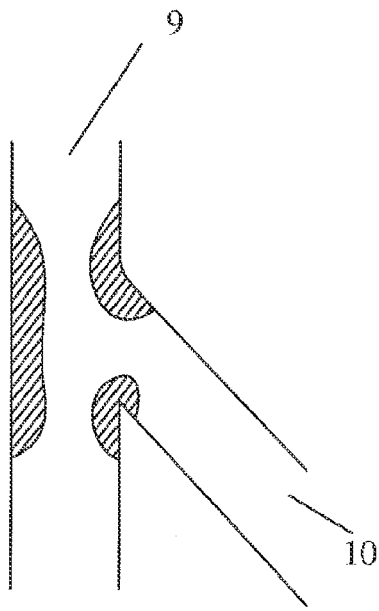
FIG. 1 is a schematic diagram of the lesion sites of a common bifurcated lesion vessel.
Figure 2:
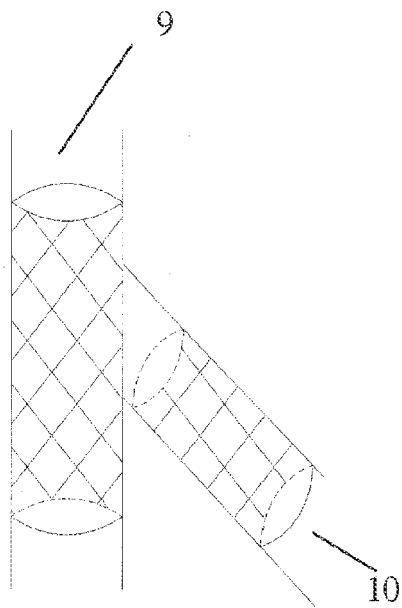
FIG. 2 is a schematic diagram of operation of the exiting stent for a branch vessel with both ends flush.
Figure 3:
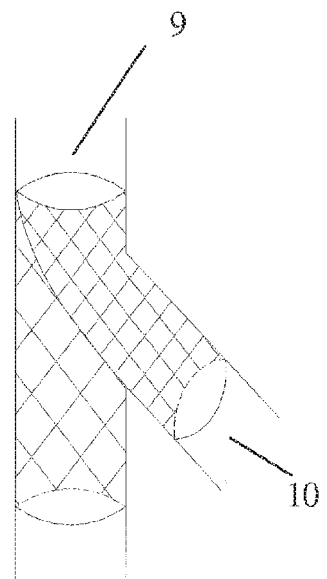
FIG. 3 is a schematic diagram of operation of the existing stent for a branch vessel adopting the "crush" technique.

In order to make those skilled in the art better understand the technical solutions in the present application, the technical solutions in the embodiments of the present application will be described clearly and completely below by taking the figures in the embodiments of the present application into consideration. Obviously, the described embodiments are only parts of the embodiments of the present application rather than all the embodiments. All the other embodiments obtained by those skilled in the art based on the embodiments in the present application without making inventive efforts should belong to the scope of protection of the present application.

FIG. 4(a)-4(d) each shows a schematic diagram of an anatomical structure of a stent for a bifurcated vessel provided by various embodiments of the present application.

As shown in FIGS. 4(a)-4(d), a stent body 1 of the stent for a bifurcated vessel comprises multiple sets of annular units 2 and connecting rods 3, each set of annular unit 2 being formed by connection of multiple undulating rods 4, and the connecting rods 3 being positioned between adjacent annular units 2 and used to connect the adjacent annular units 2. The stent body 1 has two open ends. The structure of the first open end 5 is a flush and symmetrical structure. Near the second open end 6, the length of each set of annular unit 2 is shortened by decreasing the number of the undulating rods 4 in each set of annular unit 2, or by increasing the compactness of the undulating rods 4 in each set of annular unit 2, or by performing the two simultaneously, in a direction from the middle part of the stent body 1 to the open end 6. A slope opening 7 is formed at the second open end 6, and in this case, the structure at the second open end 6 forms a slope structure taking the slope opening 7 as the slope surface by curling up the anatomical structure shown in FIG. 4(a)-4(d) or FIG. 5. In the other embodiments, the stent body 1 of the stent for a bifurcated vessel can be of the slope structure at both of the open ends.

Figure 4A:
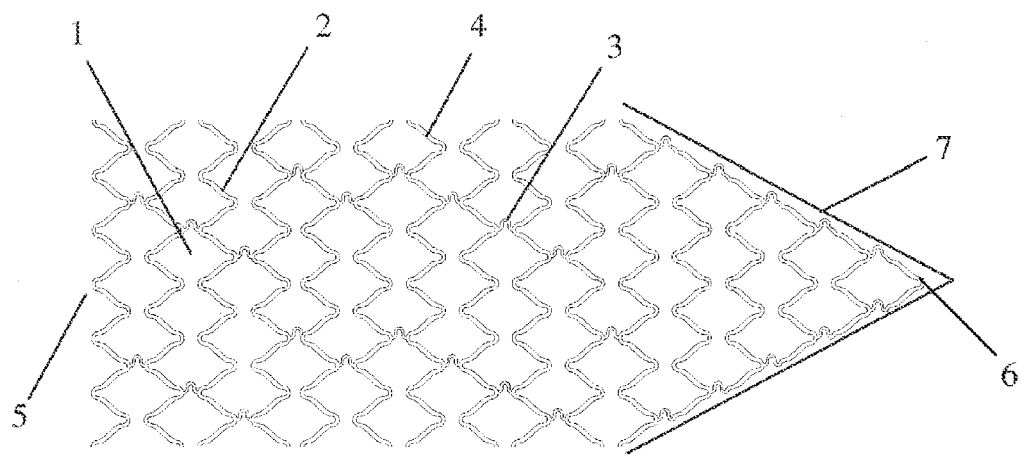
FIG. 4(a)-4(d) each shows a schematic diagram of an anatomical structure of a stent for a bifurcated vessel provided by various embodiments of the present application.
Figure 4B:
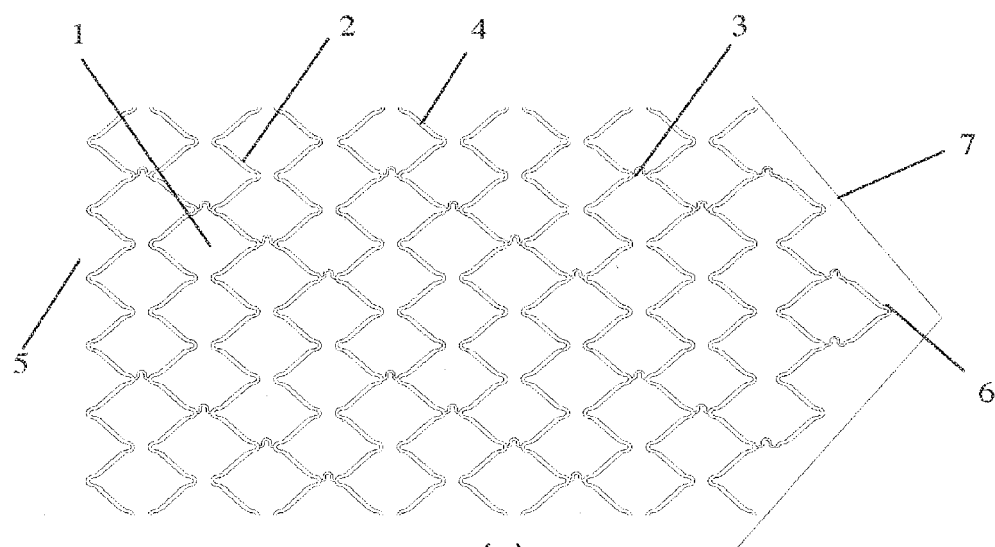

The bifurcation angle of the vessel inside the human body is generally between 0 degree to 90 degrees, and the bifurcation angles of most of the vessels branched from the bifurcation site of the vessel are about 45 degrees. In the embodiments of the present application, the axial length of the slope structure is set to 1~7 mm, and preferably 4~6 mm. Based on the set axial length of the slope structure, the angle of the slope structure, i.e. the angle between the slope surface surrounded by the slope opening 7 and the axial direction of the stent body 1, can be changed. The angel between the slope opening 7 and the axial direction of the stent body 1 can be changed by decreasing in turn the number of the undulating rods 4 in each set of annular unit 2 at one end of the stent body 1 and adjusting the length of each set of annular unit 2. At the production of the stent for a bifurcated vessel, the angle of the slope structure can be flexibly designed between 0 degree and 90 degrees so as to match with the vessels of different bifurcation angles to meet different requirements for the operation according to the condition of the bifurcation of the vessel at the application site. As shown in FIG. 4(a) and FIG. 4(b), FIG. 4(a) is a schematic diagram of the anatomical structure of the stent for a bifurcated vessel having angle of 45 degrees, and FIG. 4(b) is a schematic diagram of the anatomical structure of the stent for a bifurcated vessel having angle of 60 degrees. In an embodiment of the present application, the angle of the slope structure is preferably designed as 45 degrees, for this angle can cover most of the bifurcation angels of the vessels branched from the bifurcation site of the main vessel.

Figure 4C:
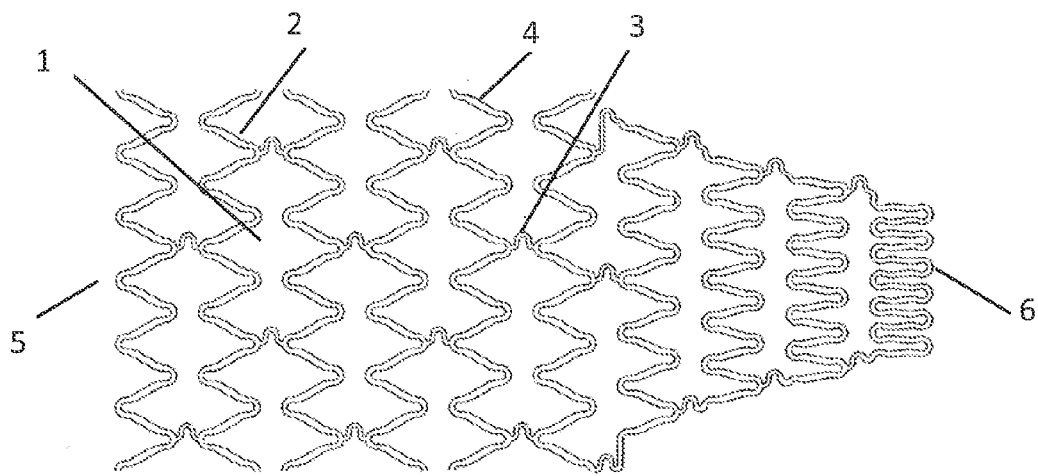

As shown in FIG. 4(c), a stent body 1 of the stent for a bifurcated vessel comprises multiple sets of annular units 2 and connecting rods 3, each set of annular unit 2 being formed by connection of multiple undulating rods 4, and the connecting rods 3 being positioned between adjacent annular units 2 and used to connect the adjacent annular units 2. The stent body 1 has two open ends. The structure of the first open end 5 is a flush and symmetrical structure. Near the second open end 6, the length of each set of annular unit 2 is shortened by increasing the compactness of the undulating rods 4 in each set of annular unit 2, in a direction from the middle part of the stent body 1 to the open end 6. A slope opening is formed at the second open end 6, and in this case, the structure at the second open end 6 forms a slope structure taking the slope opening as the slope surface by curling up the anatomical structure shown in FIG. 4(c).

Figure 4D:
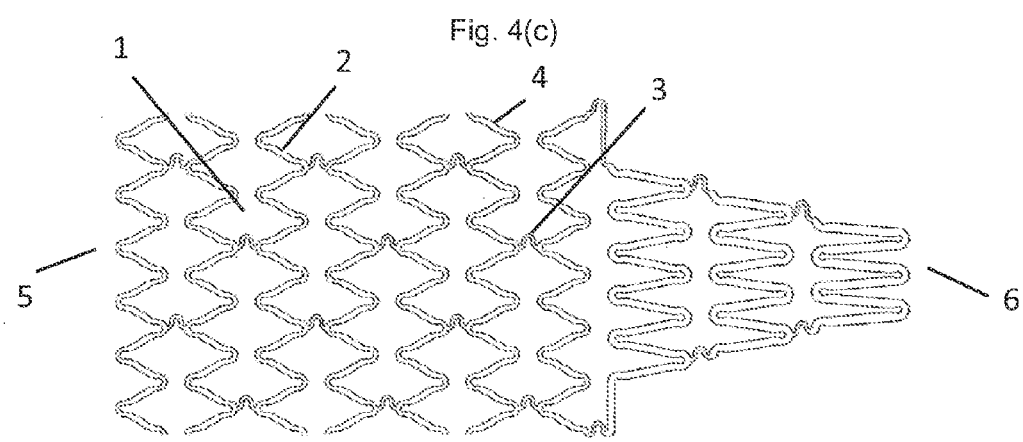

As shown in FIG. 4(d), a stent body 1 of the stent for a bifurcated vessel comprises multiple sets of annular units 2 and connecting rods 3, each set of annular unit 2 being formed by connection of multiple undulating rods 4, and the connecting rods 3 being positioned between adjacent annular units 2 and used to connect the adjacent annular units 2. The stent body 1 has two open ends. The structure of the first open end 5 is a flush and symmetrical structure. Near the second open end 6, the length of each set of annular unit 2 is shortened by decreasing the number of the undulating rods 4 in each set of annular unit 2 and increasing the compactness of the undulating rods 4 in each set of annular unit 2 simultaneously, in a direction from the middle part of the stent body 1 to the open end 6. A slope opening is formed at the second open end 6, and in this case, the structure at the second open end 6 forms a slope structure taking the slope opening as the slope surface by curling up the anatomical structure shown in FIG. 4(d).

Figure 5:
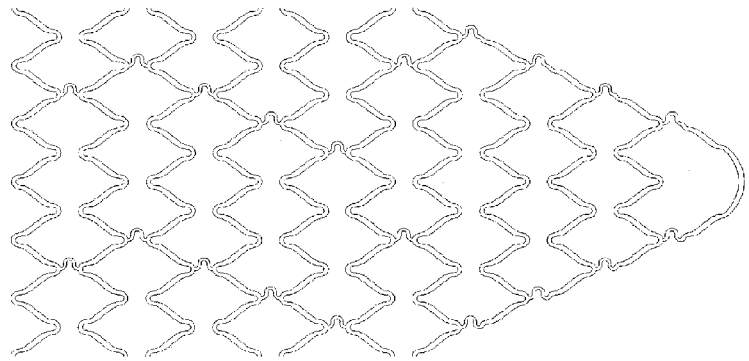
FIG. 5 is a schematic diagram of another preferable anatomical structure of a stent for a bifurcated vessel provided by an embodiment of the present application.

In the actual surgical application, in order to prevent the top (the tip close to the open end 6 is the top) of the slope opening 7 of the stent for a bifurcated vessel from piercing or scratching the inner wall of the vessel when being implanted, the top of the slope opening 7 is generally processed, and the top of the slope opening 7 is designed as a smooth arc shape or a flush shape, as shown in FIG. 5.

Figure 6A:
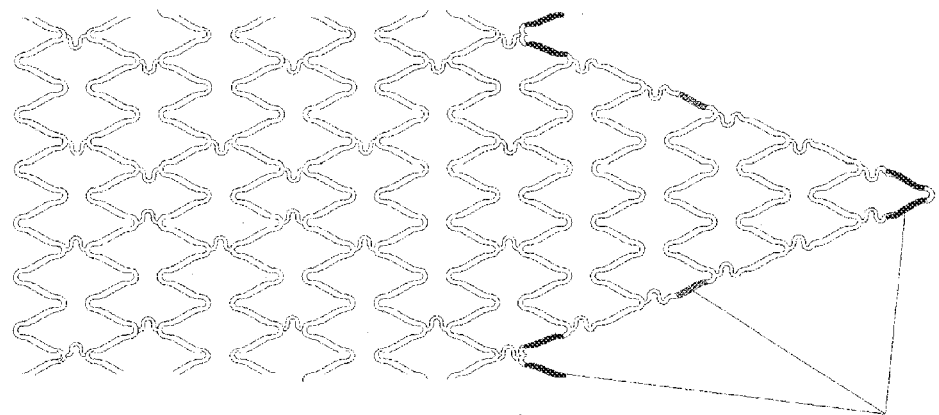
FIG. 6(a) and FIG. 6(b) are schematic diagrams of the developable marks of the stent for a bifurcated vessel provided by an embodiment of the present application.
Figure 6B:
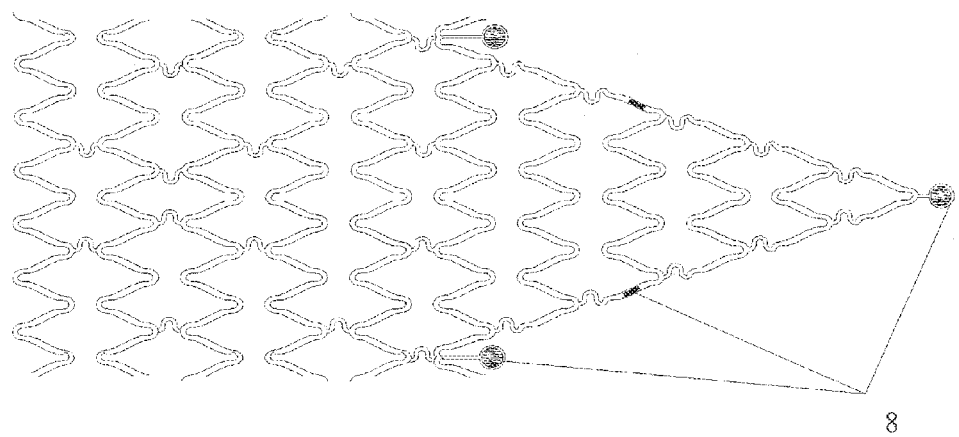

FIG. 6(a) and FIG. 6(b) are schematic diagrams of a developable mark of the stent for a bifurcated vessel provided by an embodiment of the present application.

As shown in FIG. 6(a) and FIG. 6(b), the stent for a bifurcated vessel further comprises developable marks 8, which can be developable films coated or plated on the undulating rods 4 of the stent body 1. As shown in the figures, at least four developable marks 8 are provided, wherein at least two developable marks are respectively provided on the top and bottom (the position farthest from the top in the slope surface surrounded by the slope opening 7 is the bottom) of the slope surface surrounded by the slope opening 7, and at least two other developable marks are symmetrically provided on both sides of the slope surface surrounded by the slope opening 7 along an axial center line for displaying the position of the stent for a bifurcated vessel in the surgical delivery, so that the doctor can distinguish the slope surface surrounded by the slope opening 7 in a more accurate manner and can accurately locate the stent for a bifurcated vessel during the operation. In an embodiment of the present application, the developable marks 8 can be also fixed to the stent body 1 in an embedding or winding manner. As shown in FIG. 6(*a*), the developable marks 8 can be developable wires wound on the undulating rods 4 of the stent body 1, and as shown in FIG. 6(*b*), the developable marks 8 can be developable sheet metals embedded into the undulating rods 4 of the stent body 1.

Figure 8:
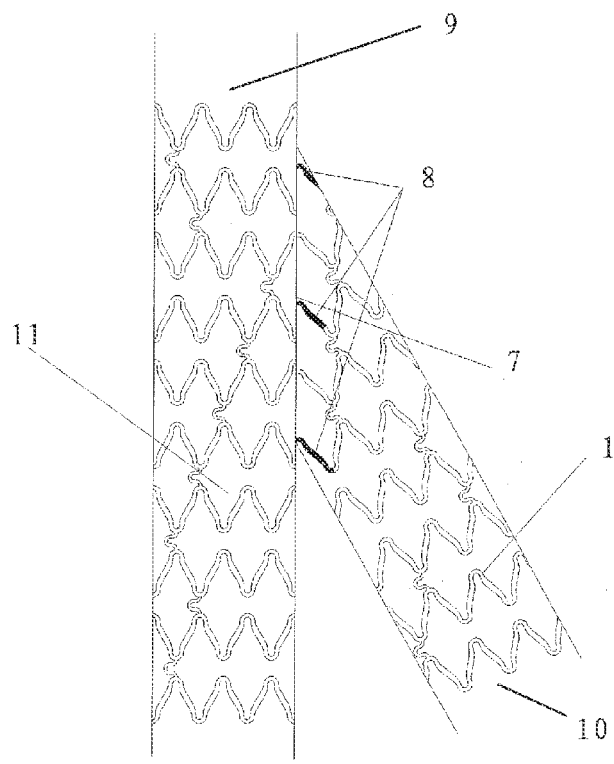
FIG. 8 is a schematic diagram of one operation of the stent for a bifurcated vessel provided by an embodiment of the present application.

FIG. 8 is a schematic diagram of one operation of the stent for a bifurcated vessel provided by an embodiment of the present application.

Figure 7:
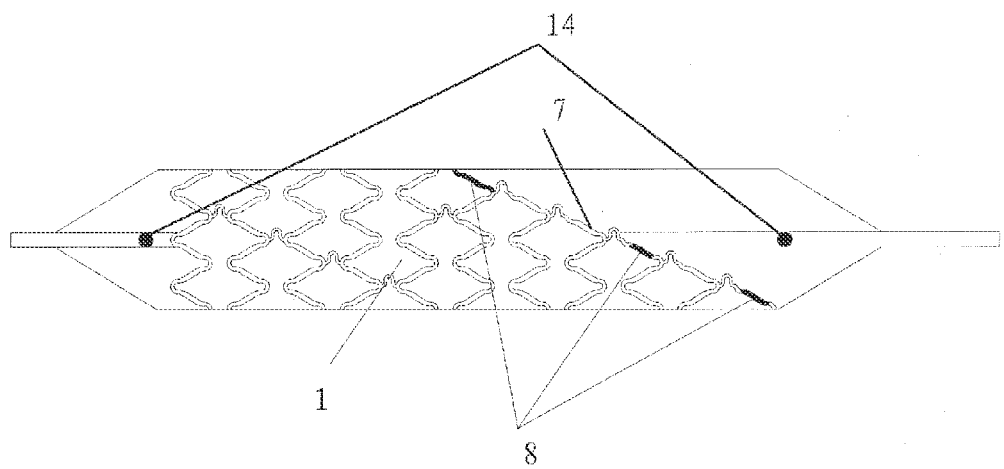
FIG. 7 is a schematic diagram of the structure where the stent for a bifurcated vessel is fixed to the balloon dilatation catheter provided by an embodiment of the present application.

As shown in FIG. 8, the lesion of vascular stenosis occurs to both the main vessel 9 and the branch vessel 10, and the reference sign 11 denotes the stent for a main vessel. The stent for a bifurcated vessel is to be used along with a balloon dilatation catheter 12 when being implanted. As shown in FIG. 7, the stent for a bifurcated vessel is firstly crimped on a balloon 13 of the balloon dilatation catheter 12 before being implanted; then the balloon dilatation catheter 12 is made to enter the branch vessel 10 from the main vessel 9 according to developable points 14 on the balloon 13; then the balloon dilatation catheter 12 is rotated according to the development positions of the developable marks 8 provided around the slope surface surrounded by the slope structure 7 in the stent body 1, so that the slope surface surrounded by the slope opening 7 in the stent body 1 joints the main vessel 9, i.e., the slope opening 7 completely contacts the main vessel 9; and finally the stent for a bifurcated vessel is released and dilated to completely cover the lesion site of the vessel, as shown in FIG. 8, to thereby achieve the implanting process.

Figure 9:
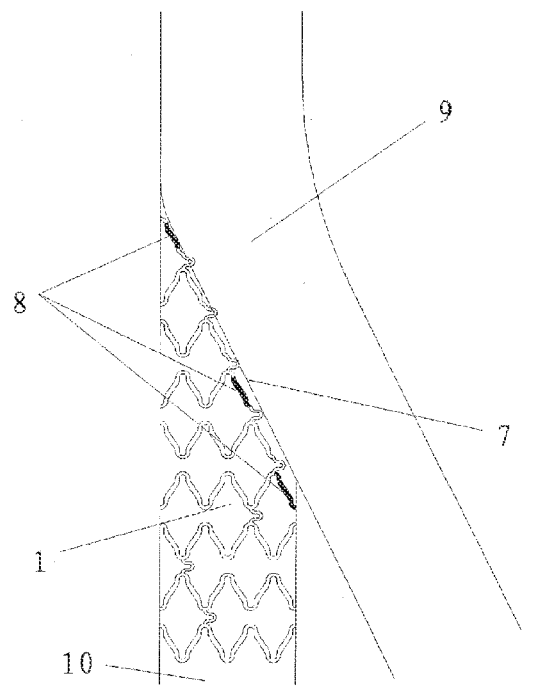
FIG. 9 is a schematic diagram of another operation of the stent for a bifurcated vessel provided by an embodiment of the present application.

FIG. 9 is a schematic diagram of another operation of the stent for a bifurcated vessel provided by an embodiment of the present application.

As shown in the figure, the lesion of vascular stenosis occurs to the branch vessel 10 only, and the main vessel 9 is normal. The implanting process of the stent for a bifurcated vessel is the same as the above implanting process, and the state after the implantation is as shown in FIG. 9.

In the embodiments of the present application, at least one end of the stent for a bifurcated vessel, the number of the undulating rods in each set of annular unit is decreased in turn, or the compactness of the undulating rods in each set of annular unit is increased in turn, or the two are performed simultaneously, in a direction from the middle part of the stent body to the open end having the slope structure, to shorten the length of each set of annular unit in turn to form a slope structure. The angle of the slope structure matches with the bifurcation angle of the branch vessel. Thus, the stent for a bifurcated vessel can completely and sufficiently cover the vessel at the lesion site and will not overlap the stent for a main vessel after being implanted in the lesion site of the bifurcated vessel of the human body.

In addition, at least four developable marks are provided around the slope surface of the slope structure of the stent for a bifurcated vessel. In the at least four developable marks, at least two developable marks are respectively provided at the top and bottom of the slope structure, and at least two other developable marks are symmetrically provided on both sides of the slope surface of the slope structure along an axial center line. In the delivering process, the doctor can clearly distinguish the slope surface of the slope structure of the stent for a bifurcated vessel according to the development positions of the developable marks, and then the doctor rotates the stent by rotating a balloon dilatation catheter, so that the slope surface of the slope structure can joint the main vessel, and then releases and dilates the stent. Thus, this stent for a bifurcated vessel can be also located accurately in the delivering and releasing process to facilitate the surgical procedure by the doctor.

The above contents are only preferred embodiments of the present invention and enable those skilled in the art to understand or achieve the present invention. Multiple amendments to these embodiments are obvious to those skilled in the art, and general principles defined in this application can be achieved in the other embodiments in case of not breaking away from the spirit or scope of the present invention. Thus, the present invention will be not limited to these embodiments shown in this application, but shall accord with the widest scope consistent with the principles and novel characteristics disclosed by this application.

The invention claimed is:

1. A stent for a bifurcated vessel, comprising:
    a stent body having a first open end and a second open end opposite to each other, the stent body comprises:
        a plurality of body segments, each of the plurality of body segments including a plurality of wave members connected to each other in an undulating manner;
        two or more connecting rods positioned between adjacent body segments and configured to connect the adjacent body segments;
    a slope structure formed at least at the second open end of the stent body, the slope structure having a configuration where (1) compactness of the wave members increases in the direction from the middle part of the stent body toward the second open end, or (2) a number of the wave members in the plurality of body segments decreases and the compactness of the wave members increases in the direction from the middle part of the stent body toward the second open end.

2. The stent for a bifurcated vessel according to claim 1, wherein an axial length of the slope structure is 1~7 mm.

3. The stent for a bifurcated vessel according to claim 1, wherein a diameter of the stent is 2.25 mm~4.0 mm.

4. The stent for a bifurcated vessel according to claim 3, wherein a material of the stent body includes a stainless steel, a cobalt-chromium alloy, a nickel-based alloy, a degradable magnesium alloy or a polymer material.

5. The stent for a bifurcated vessel according to claim 1, wherein a top of the slope structure is of a smooth arc shape or a flush shape.

6. The stent for a bifurcated vessel according to claim 1, wherein the number of the wave members in the plurality of body segments forming the slope structure remains unchanged in a direction from a middle part of the stent body to the second open end having the slope structure.

7. The stent for a bifurcated vessel according to claim 1, wherein at least four developable marks are further provided around a slope surface of the slope structure, wherein at least two developable marks are respectively provided at the top and bottom of the slope surface of the slope structure, and at least two other developable marks are symmetrically provided on both sides of the slope surface along an axial center line.

8. The stent for a bifurcated vessel according to claim 7, wherein an included angle between the slope surface of the slope structure and an axial direction of the stent body is between 0 degrees and 90 degrees.

9. The stent for a bifurcated vessel according to claim 1, wherein an included angle between a slope surface of the slope structure and an axial direction of the stent body is 45 degrees.

10. The stent for a bifurcated vessel according to claim 9, wherein an axial length of the slope structure is 4~6 mm.

* * * * *